(12) United States Patent
Wong et al.

(10) Patent No.: US 7,335,193 B2
(45) Date of Patent: Feb. 26, 2008

(54) OSMOTICALLY-DRIVEN FLUID DISPENSER

(75) Inventors: Patrick S. L. Wong, Burlingame, CA (US); Nipun Davar, Fremont, CA (US)

(73) Assignee: Durect Corporation, Cupertino, CA (US)

( * ) Notice: Subject to any disclaimer, the term of this patent is extended or adjusted under 35 U.S.C. 154(b) by 182 days.

(21) Appl. No.: 10/885,188

(22) Filed: Jul. 6, 2004

(65) Prior Publication Data
US 2005/0043457 A1    Feb. 24, 2005

Related U.S. Application Data

(62) Division of application No. 09/772,815, filed on Jan. 30, 2001, now abandoned.

(60) Provisional application No. 60/180,395, filed on Feb. 4, 2000.

(51) Int. Cl.
*A61K 9/22* (2006.01)

(52) U.S. Cl. .................. 604/892.1; 604/890.1

(58) Field of Classification Search ............. 604/892.1, 604/131–133, 218, 93.01, 890.1, 140–143, 604/15; 128/832; 424/422–424, 427, 430, 424/457, 468
See application file for complete search history.

(56) References Cited

U.S. PATENT DOCUMENTS

| | | | |
|---|---|---|---|
| 2,860,110 A | 11/1958 | Godshalk | |
| 3,125,458 A | 3/1964 | Dalton | |
| 3,300,327 A | 1/1967 | Smith et al. | |
| 3,366,586 A | 1/1968 | Crowley et al. | |
| 3,429,840 A | 2/1969 | Lowe, Jr. et al. | |
| RE27,280 E | 2/1972 | Manjikian | |
| 3,648,845 A | 3/1972 | Riley | |
| 3,663,278 A | 5/1972 | Blose et al. | |
| 3,720,321 A | 3/1973 | Coughlin et al. | |
| 3,760,984 A | 9/1973 | Theeuwes | |
| 3,853,563 A | 12/1974 | Depoorter et al. | |
| 3,917,777 A | 11/1975 | Asada et al. | |
| 3,925,096 A | 12/1975 | Kartov | |
| 3,929,693 A | 12/1975 | Hochberg | |
| 3,995,631 A | 12/1976 | Higuchi | |
| 4,046,843 A | 9/1977 | Sano et al. | |
| 4,111,202 A * | 9/1978 | Theeuwes | ................ 604/892.1 |
| 4,239,545 A | 12/1980 | Uemura et al. | |
| 4,256,805 A | 3/1981 | Tugukuni et al. | |
| 4,305,823 A | 12/1981 | Batzer et al. | |
| 4,305,824 A | 12/1981 | Uemura et al. | |
| 4,320,758 A * | 3/1982 | Eckenhoff et al. | ....... 604/892.1 |
| 4,503,030 A | 3/1985 | Edgren | |
| 4,519,801 A | 5/1985 | Edgren | |
| 4,522,625 A | 6/1985 | Edgren | |
| 4,553,973 A | 11/1985 | Edgren | |

(Continued)

FOREIGN PATENT DOCUMENTS

CA    949513    6/1974

*Primary Examiner*—Kevin C. Sirmons
*Assistant Examiner*—Laura C. Schell

(57) ABSTRACT

Improvements in a mini-osmotic pump and coating compositions are described. The dispensing pump includes an inner fluid-filled bag encased by an osmotic layer and outer, semi-permeable membrane. The inner bag is formed with an arcuate edge at the open end of the bag to inhibit formation of fissures in the outer membrane in this edge region. The coating compositions include cellulose acetate butyrate, cellulose acetate propionate, and polymethylmethacrylate polymers, optionally mixed with ethyl cellulose in acetone based solvent systems.

14 Claims, 3 Drawing Sheets

U.S. PATENT DOCUMENTS

| | | |
|---|---|---|
| 4,576,604 A | 3/1986 | Guittard et al. |
| 4,578,075 A | 3/1986 | Urquhart et al. |
| 4,627,850 A | 12/1986 | Deters et al. |
| 4,638,022 A | 1/1987 | Cope |
| 4,777,049 A | 10/1988 | Magruder et al. |
| 4,783,337 A | 11/1988 | Wong et al. |
| 4,863,744 A | 9/1989 | Urquhart |
| 4,877,528 A | 10/1989 | Friesen et al. |
| 4,883,593 A | 11/1989 | Friesen et al. |
| 4,891,248 A | 1/1990 | Kraus |
| 4,920,465 A | 4/1990 | Sargent |
| 4,929,233 A * | 5/1990 | Roth et al. .................. 604/131 |
| 4,946,686 A | 8/1990 | McClelland et al. |
| 4,946,687 A | 8/1990 | Ayer et al. |
| 4,948,592 A | 8/1990 | Ayer et al. |
| 5,019,396 A | 5/1991 | Ayer et al. |
| 5,208,037 A | 5/1993 | Wright et al. |
| 5,232,705 A | 8/1993 | Wong et al. |
| 5,279,608 A * | 1/1994 | Cherif Cheikh ......... 604/892.1 |
| 5,306,739 A | 4/1994 | Lucey |
| 5,312,862 A | 5/1994 | Nielsen |
| 5,324,280 A | 6/1994 | Wong et al. |
| 5,331,027 A | 7/1994 | Whitbourne |
| 5,413,572 A | 5/1995 | Wong et al. |
| 5,977,217 A | 11/1999 | Socci et al. |
| 6,429,248 B2 | 8/2002 | Schwark et al. |

* cited by examiner

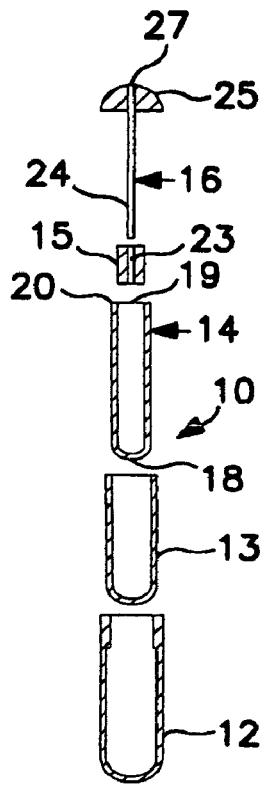
FIG. 1
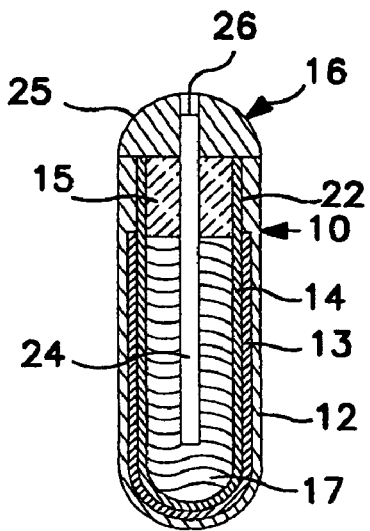
FIG. 2
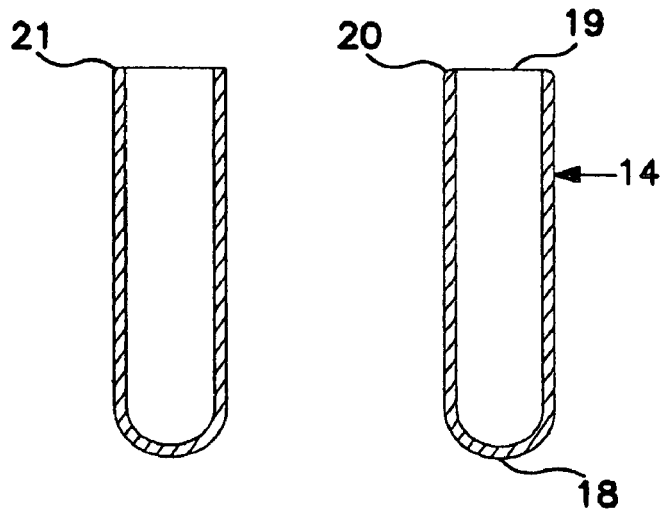
FIG. 4 PRIOR ART
FIG. 3
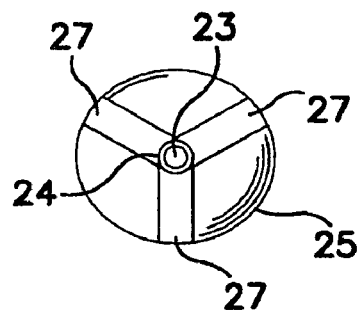
FIG. 5

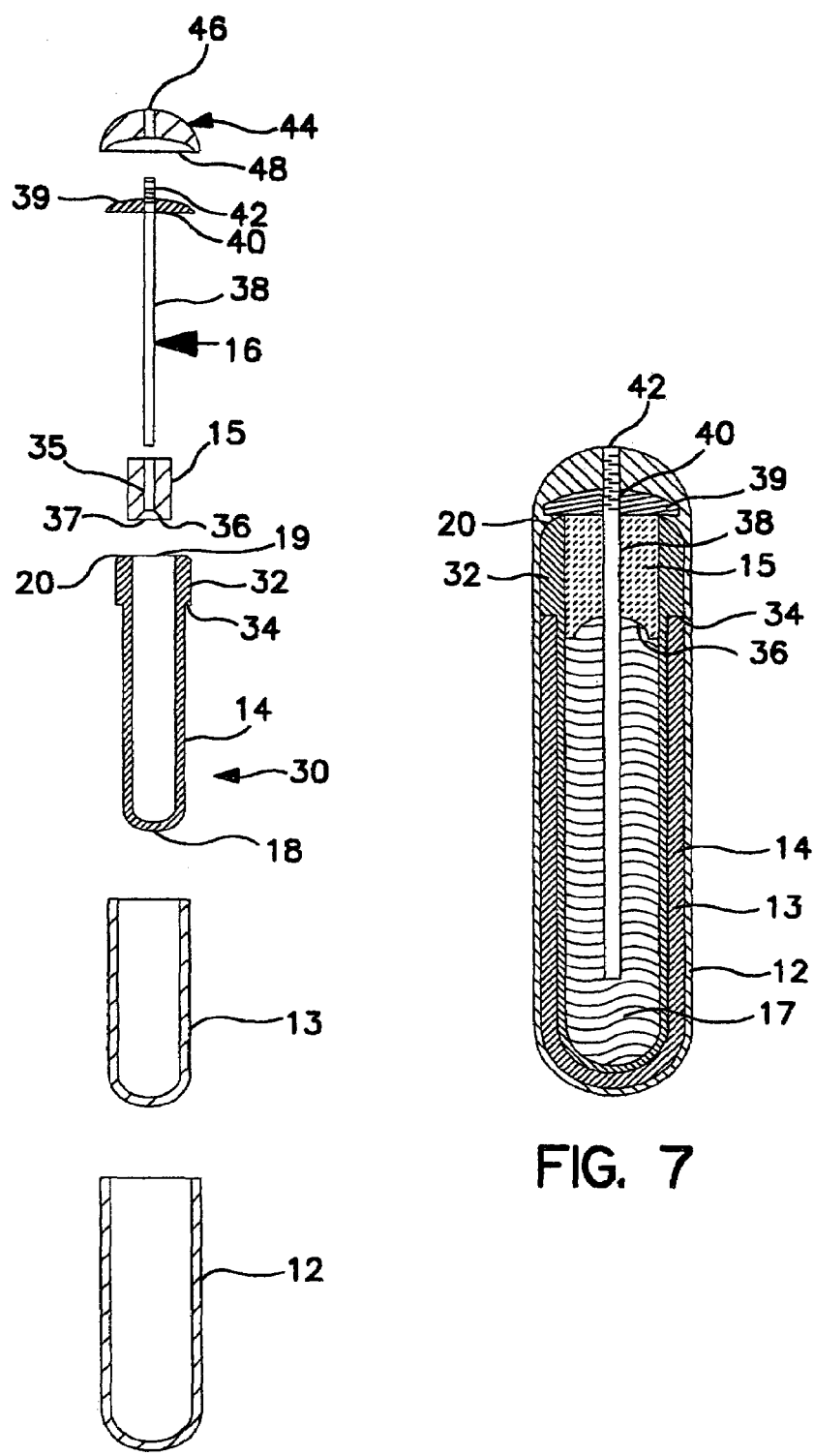

OSMOTICALLY-DRIVEN FLUID DISPENSER

CROSS-REFERENCE TO RELATED APPLICATIONS

"This application claims the priority of U.S. Provisional Application Ser. No. 60/180,395, filed Feb. 4, 2000, which is incorporated herein by reference. This application is also a divisional of application Ser. No. 09/772,815, filed Jan. 30, 2001, which is now abandoned."

BACKGROUND OF INVENTION

1. Field of the Invention

The present invention relates to improvements and modifications of an osmotically driven fluid dispenser and coating compositions for osmotically driven dispensers.

2. Description of the Related Art

Osmotically driven dispensers are described in commonly owned U.S. Pat. Nos. 3,760,984 and 4,320,758, which are hereby incorporated by reference in their entirety. The mini-osmotic pumps described in these patents as well as in the present invention are osmotically driven dispensers sized for use as therapeutic systems for administering drugs to animals and humans. The basic components of the pumps are an inner flexible bag that holds the drug charge; an intermediate layer of an osmotically effective solute composition, such as an inorganic salt, that encapsulates the bag; an outer shape-retaining membrane that is permeable to water and that encapsulates both the layer of osmotically effective solute composition and the encapsulated bag; and a filling/discharge port that communicates with the interior of the bag.

In operation, the bag is filled with drug via the filling/discharge port and placed in an aqueous environment, such as a body cavity or within body tissue. Water is imbibed from the environment by the osmotically effective solute through the membrane into the space between the inner flexible bag and the membrane. Since the bag is flexible and the membrane is rigid, the imbibed water enlarges the space between the membrane and the bag and exerts an inwardly squeezing pressure on the bag thereby displacing drug out of the bag through the filling/discharge port.

One shortcoming of the above-described pumps is the tendency to develop cracks in the region of the seal between the inner bag and the outer membrane. This tendency is pronounced when the outer membrane is formed from solvent-polymer mixtures in which the polymer is relatively less soluble. However, use of such solvents may be desirable due to safety and waste management concerns. Formation of fissures in the outer membrane in the region of the joint between the open end of the inner bag results in decreased performance or complete failure of the pump, evidenced by a decreased or non-constant flow rate or an absence of flow. The present invention is directed towards eliminating or reducing this shortcoming.

SUMMARY OF INVENTION

In one aspect, the invention includes an improvement in a mini-osmotic pump. The pump dispenser of the invention comprises (i) an inner flexible container adapted to contain a fluid to be dispensed, said inner bag having an open end, (ii) an intermediate layer of an osmotically effective solute composition at least partly encapsulating the bag, (iii) an outer, shape-retaining membrane encapsulating the layer of osmotically effective solute composition, said membrane being at least in part permeable to water, (iv) a port that extends from the interior of the bag to the exterior of the dispenser through which the fluid may be charged into the bag and dispensed from the bag, and (v) a cap adapted for sealing engagement with the open end of the inner bag. The improvement comprises modifying the open end of the inner bag to have an arcuate edge.

In another aspect, the invention includes improved coating compositions from which the outer, shape-retaining membrane may be formed. The coating compositions may be mixtures of polymers with acetone or acetone-based solvent mixtures. Such coating compositions find utility not only in the osmotically driven devices described herein but in other osmotically driven drug delivery systems that have been described in the patent and technical literature.

Accordingly, the invention comprises in other aspects, a coating composition comprising a mixture of (i) polymer selected from the group consisting of cellulose acetate butyrate, cellulose acetate propionate, polymethylmethacrylate, mixtures thereof, and mixtures of the foregoing with ethyl cellulose, (ii) solvent selected from the group consisting of acetone, mixtures of acetone and water and mixtures of acetone and lower alkanols having 1-8 carbon atoms, and optionally one or more additives selected from the group consisting of plasticizers and flux enhancers. The lower alkanols may be straight or branched chain, and are illustrated by representative alcohols such as methanol, ethanol, isopropyl alcohol, and the like. Typically, the concentration of acetone in the solvent is at least 80% by volume, and the polymer concentration in the solvent is between 1-15% (w/v). The coating compositions of the invention typically provide for formed semipermeable membrane coats exhibiting a water transmission rate of between 1-60 cc·mil/cm$^2$·hr.

These and other objects and features of the invention will be more fully appreciated when the following detailed description of the invention is read in conjunction with the accompanying drawings.

BRIEF DESCRIPTION OF SEVERAL VIEW OF THE DRAWINGS

FIG. 1 is an elevational, exploded, sectional view of one embodiment of the osmotic pump dispenser of the invention;

FIG. 2 is an enlarged sectional view of the pump dispenser of FIG. 1;

FIG. 3 is an enlarged sectional view of the inner bag of the dispenser of FIG. 1;

FIG. 4 is an enlarged sectional view of a prior art inner bag;

FIG. 5 is an enlarged, top plan view of the flow moderator of the dispenser of FIG. 1;

FIG. 6 is an elevational, exploded, partly sectional view of another embodiment of the dispenser of the invention;

FIG. 7 is an enlarged, sectional view of the dispenser of FIG. 6; and

DETAILED DESCRIPTION OF THE INVENTION

Figure 8:
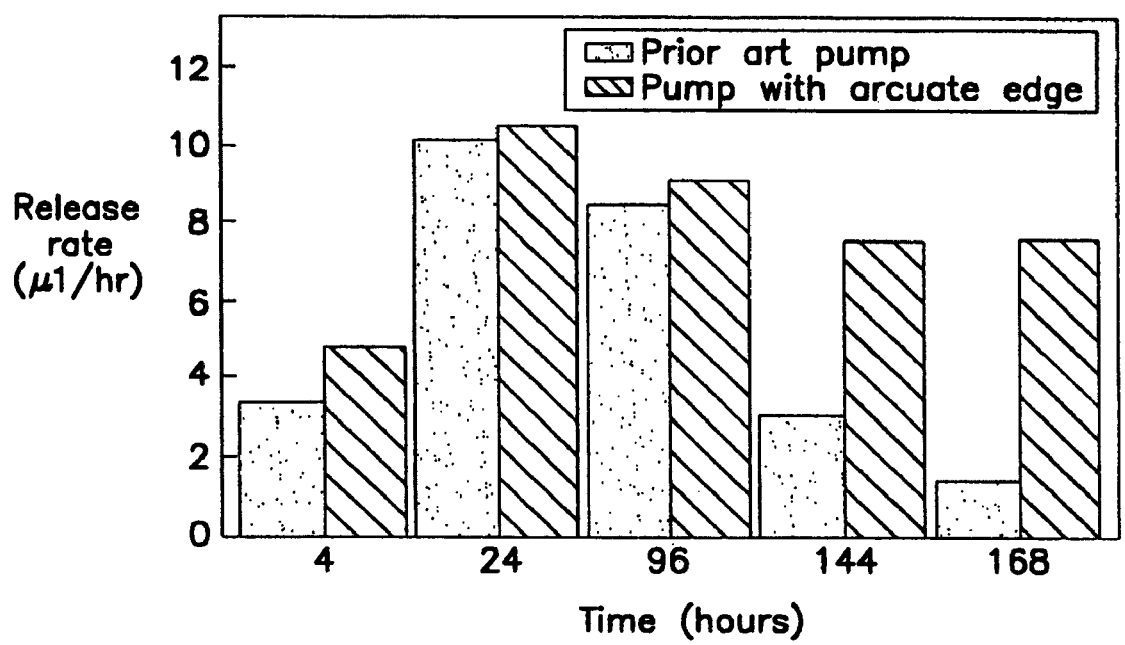
FIG. 8 is a bar graph showing the release rate in μl/hr, of fluid from a pump in accordance with the invention (dotted bars) and a prior art pump (bars with dashes).

FIGS. 1 and 2 illustrate an osmotically driven fluid dispenser, generally designated 10. The basic components of dispenser 10 are an outer, shape-retaining, semipermeable membrane 12, an intermediate layer 13 of an osmotically effective solute, an inner, flexible container 14, a plug 15, and a flow moderator, generally designated 16.

Container 14 may be formed as a bag adapted to contain a fluid composition, such as an active agent composition 17, as best seen in FIG. 2, in fluid form. The term "active agent" as used herein means any compound or mixture of compounds that can be dispensed to produce a predetermined beneficial and useful result. Exemplary active agents are recited in co-owned U.S. Pat. No. 4,320,758 at Col. 2, lines 24-37, incorporated by reference hereinbefore. The term "bag" means any suitable container having a closed end and an open end, as described more fully below.

In order to be a suitable container for the fluid, bag 14 should be substantially impermeable to the therapeutic composition and be compatible with the therapeutic composition. By "compatible", it is meant that the bag should not be corroded, solubilized, or otherwise affected deleteriously by the composition. Additionally, when the composition is a drug or the like, the composition should not be significantly contaminated by the bag, such as by the extraction of leachables from the material forming the bag. Bag 14 may be made from elastomeric compositions that may be formed into thin sheets. The elastomeric properties of the bag composition and the thickness of the bag wall should be such as to cause the bag to readily collapse inwardly when a force is applied to the bag exterior. Such elastomeric compositions are disclosed in commonly owned U.S. Pat. No. 3,760,984 at Col. 5, line 40 to Col. 7, line 37, fully incorporated by reference hereinbefore, and in commonly owned Canadian Pat. No. 949,513 at p. 10, line 28 to p. 11, line 7, which disclosure is incorporated herein by reference.

Bag 14 is elongated and generally cylindrical and is closed at its end 18 and open at its opposite end 19. According to an important feature of the invention, edge 20 at open end 19 of the bag is arcuate, as seen best in the exploded view of the inner bag in FIG. 3. The curvature of edge 20 can be selectively varied as long as the edge forms no sharp points, as does the edge 21 with a 90° angle of the prior art bag seen in FIG. 4. The arcuate edge significantly reduces the development of cracks or fissures in the outer membrane 12. Accordingly, in a preferred embodiment of the invention, edge 20 of the inner bag is at an angle of other than 90°, and in a preferred embodiment has an angle of less than 90°. In terms of radius of curvature, in a preferred embodiment of the invention edge 20 has a radius of curvature of greater than 0.01 inches (0.254 mm), even more preferably a radius of curvature of greater than 0.02 inches (0.508 mm). The upper boundary of the radius of curvature of the edge is less critical, since, as indicated above, the important feature is that the edge have curvature, and a highly curved edge, thus a high radius of curvature, will also serve to minimize the development of fissures. Devices may be manufactured where the radius of curvature of the edge of concern is in the range of 0.08 inches (2.03 mm) to 0.09 inches (2.29 mm). Thus, in one embodiment a device having a edge with a radius of curvature between 0.01-0.09 inches (0.254-2.29 mm), more preferably between 0.01-0.08 inches (0.254-2.03 mm), and still more preferably between 0.01-0.07 inches (0.254-1.78 mm) is contemplated.

Returning now to FIGS. 1 and 2, bag 14 is partly encapsulated by layer 13 of an osmotically effective solute composition such that a band 22 of the exterior of bag 14 proximate to open end 19 is not covered by layer 13. The purpose of layer 13 is to imbibe water across membrane 12 into the space between the exterior of bag 14 and the inner surface of membrane 12, that is, the space occupied by layer 13. Osmotically effective solute compositions that may be used to form layer 13 are disclosed in U.S. Pat. No. 3,760,984 at Col. 7, line 38 to Col. 8, line 2 and in Canadian Pat. No. 949,513 at p. 18, lines 22-27 and in U.S. Pat. No. 4,320,758 at Col. 3, line 2 to line 38, which disclosures were incorporated by reference hereinbefore.

Solute layer 13 is in turn encapsulated by outer membrane 12. Membrane 12 also covers band 22 and forms a fluid tight seal therewith. At least a part of membrane 12 is permeable to water. Preferably all of membrane 12 is permeable to water. Membrane 12 is impermeable to the osmotically effective solute composition. Membrane 12 is also shape-retaining; that is, it is sufficiently rigid to be substantially undeformed by the hydrostatic pressure that is generated in the space between its inner surface and the exterior of bag 14 by the water imbibed by layer 13. The thickness and composition of membrane 12 affects the rate at which water will be imbibed through it by solute layer 13. Such membranes and compositions that may be used to form them are disclosed in U.S. Pat. No. 3,760,984 at col. 4, line 53 to col. 5, line 39 and in Canadian Pat. No. 949,513 at p. 9, line 24 to p. 10, line 27, which disclosures have been incorporated by reference hereinbefore. However, preferred membranes are those formed from cellulose acetate butyrate, cellulose acetate propionate, and polymethylacrylate, either alone or in mixtures with each other, and optionally in mixture with ethyl cellulose, that are deposited out of acetone-based solvent systems that are described in greater detail hereinafter. Such preferred membranes are useful not only with the osmotically-driven pump described herein, but are useful generally with osmotic systems known in the art that utilize semipermeable membranes. The outer membrane thickness typically will be between 0.001-0.050 inches (0.0254 millimeters-1.27 millimeters), and preferably 0.004-0.030 inches (0.102 millimeters-0.762 millimeters).

It will be appreciated that outer membrane 12 can include, if desired, a plasticizer to lend flexibility to the membrane. Plasticizers are well known to those of skill in the art and include, for example, triethyl citrate, tributyl citrate and polaxamers (brand name PLURONIC, product of BASF Corp., Mt. Olive, N.J.). Other materials for imparting flexibility and elongation properties to the membrane, for making the membrane less-to-nonbrittle and to render tear strength, include phthalate plasticizers such as dibenzyl phthalate, dihexyl phthalate, butyl octyl phthalate, straight chain phthalates of six to eleven carbons, di-isononyl phthalate, di-isodecyl phthalate, and the like. The plasticizers include nonphthalates such as triacetin, dioctyl azelate, epoxidized tallate, tri-isoctyl trimellitate, tri-isononyl trimellitate, sucrose acetate isobutyrate, epoxidized soybean oil, and the like. The amount of plasticizer in the membrane when incorporated is about 0.01% to 20% weight.

The outer membrane may also contain flux regulating agents. The flux regulating agent is a compound added to assist in regulating the fluid permeability or flux through the membrane. The flux regulating agent can be a flux enhancing agent or a decreasing agent. The agent can be preselected to increase or decrease the liquid flux. Agents that produce a marked increase in permeability to fluid such as water, are often essentially hydrophilic, while those that produce a marked decrease to fluids such as water, are essentially hydrophobic. The amount of regulator in the membrane when incorporated therein generally is from about 0.01% to 20% by weight or more. The flux regulator agents in one embodiment that increase flux include polyhydric alcohols, polyalkylene glycols, polyalkylenediols, polyesters of alkylene glycols, and the like. Typical flux enhancers include polyethylene glycol 300, 400, 600, 1500, 4000, 6000 and the like; low molecular weight gylcols such as polypropylene glycol, polybutylene glycol and polyamylene glycol: the polyalkylenediols such as poly(1,3-propanediol), poly(1,4-butanediol), poly(1,6-hexanediol), and the like; aliphatic diols such as 1,3-butylene glycol, 1,4-pentamethylene glycol, 1,4-hexamethylene glycol, and the like; alkylene triols such as glycerine, 1,2,3-butanetriol, 1,2,4-hexanetriol, 1,3,6-hexanetriol and the like; esters such as ethylene glycol dipropionate, ethylene glycol butyrate, butylene glycol dipropionate, glycerol acetate esters, and the like. Representative flux decreasing agents include phthalates substituted with an alkyl or alkoxy or with both an alkyl and alkoxy group such as diethyl phthalate, dimethoxyethyl phthalate, dimethyl phthalate, and di(2-ethylhexyl) phthalate, aryl phthalates such as triphenyl phthalate, and butyl benzyl phthalate; insoluble salts such as calcium sulphate, barium sulphate, calcium phosphate, and the like; insoluble oxides such as titanium oxide; polymers in powder, granule and like form such as polystyrene, polymethylmethacrylate, polycarbonate, and polysulfone; esters such as citric acid esters esterified with long chain alkyl groups; inert and substantially water impermeable fillers; resins compatible with cellulose based wall forming materials, and the like.

Plug 15 fits into the open end 19 of bag 14. Plug 15 is generally cylindrical and is approximately as long as band 22. The exterior of plug 15 forms a fluid tight seal with the portion of the interior surface of bag 14 with which it is in contact. Plug 14 has an axial, central bore 23 extending completely through it. Bore 23 provides access to the interior of bag 14 for filling bag 14 with composition agent 17. Bore 23 is also adapted to receive flow moderator 16. Plug 15 may be made from the same materials as are used to make flexible bag 14; however, the dimensions of plug 15 should be such that it is substantially inflexible.

Flow moderator 16 provides the passageway from the interior of bag 14 to the exterior of dispenser 11 by which composition 17 is discharged from dispenser 11. Flow moderator 16 comprises a conduit, in the form of a rigid cylindrical tube 24, and a head or cap 25. Tube 24 and head 25 may be made from suitable plastics or metals, respectively. The outer diameter of tube 24 is approximately the same as the diameter of bore 23 such that tube 24 may be inserted through bore 23 into bag 14 with tube 24 fitting snugly within bore 23 so as to form an essentially fluid tight seal with plug 15. The length of tube 24 is such that it extends into bag 14 to at least about 50% of the elongated dimension of the interior of bag 14, i.e., the distance from the inner side of end 18 to the inner end of plug 15. Preferably tube 24 extends into bag 14 over substantially the entire, but not all of (say 85% to 95%), of said elongated dimension. The inner diameter of tube 24 is correlated to the length of tube 24 such that substantial diffusional flow of composition 17 through tube 24 will not occur. Tube 24 is, in effect, a capillary that provides resistance to the flow of composition 17, thereby reducing or eliminating bulk loss of composition 17 from the outlet port of dispenser 11. Although not shown in the drawings, tube 24 may extend outwardly from the exterior of head 25 to provide a site for attachment of a catheter or other dispensing means. Head 25 is preferably hemispherical and has a diameter approximately equal to the outer diameter of dispenser 10. It also has a diametrical bore 26 for receiving tube 24. As seen in FIG. 2, the flat side of head 25 fits against the top of plug 15 and the top edge of bag 14. Thus the spherical surface of head 25 provides a smooth, blunt surface that generally aligns with the exterior surface of the bag-solute layer-membrane assembly, which bluntness and alignment are desirable if the dispenser is to be used as an implant to administer drugs to animals or humans.

With reference now to FIG. 5, head 25 has three radial, equispaced grooves 27 in its spherical surface that intersect at bore 26. The outer end of tube 24 is inset slightly from the spherical surface of head 25 (FIG. 2) and thus grooves 27 serve as flow channels for composition 17 exiting from the outer end of tube 24.

FIGS. 6 and 7 illustrate an osmotic dispenser according to another embodiment of the invention. The dispenser of FIGS. 6 and 7, generally designated 30, is nearly identical to dispenser 10 of FIGS. 1 and 2, and like components are identified with like numerals. Dispenser 30 differs from dispenser 10 in the design of the inner bag 14, the flow modulator 16 and the plug 15, as will now be described.

Bag 14 is elongated and generally cylindrical and is closed at its end 18 and open at its opposite end 19. The edge 20 at open end 19 is a smooth, curved surface, as described above with respect to dispenser 10. The wall of bag 14 is thickened outwardly at 32 to form a shoulder 34. As seen in FIG. 7, the portion of the exterior of bag 14 below shoulder 34 is encapsulated by sleeve 13 whose wall is approximately as thick as shoulder 34 is wide. Sleeve 13 is encapsulated by outer membrane 12. Membrane 12 also covers the exterior of the portion of bag 14 above shoulder 34 and covers the arcuate edge 20 to form a fluid tight seal in this region.

Plug 15 fits into the open end 19 of bag 14. Plug 15 is generally cylindrical and is approximately as long as the thickened portion of bag 14 above shoulder 34. The exterior of plug 15 forms a fluid tight seal with the portion of the interior surface of bag 14 with which it is in contact. Plug 15 has an axial, central bore 35 extending completely through it. Bore 35 provides access to the interior of bag 14 for filling bag 14 with active agent composition 17. Bore 35 is also adapted to receive flow moderator 16. Plug 15 preferably has a hemispherically shaped recess 36 in its inner (bottom) end 37. The presence of such a recess or concavity in end 37 reduces the likelihood of entrapping air in bag 14 when filling bag 14 with composition 17. The plug described with respect to dispenser 10 was generally cylindrical in shape, its inner end joining the wall of the bag at a 90° angle. During the filling of the bag, the fluid has a natural tendency, due to its high surface tension, to form a curved surface beginning near the top of the wall of the bag and continuing up to the filling/discharge port. This curvature causes an air pocket at the intersection of the wall of the bag and the plug. The plug of dispenser 30 has a hemispherically recessed lower surface, curved to substantially match the arc created by the surface tension of the drug solution during the filling process. This reduces the volume of the dispenser that cannot be filled due to air entrapment from approximately 15% to less than 2% to 3%.

Flow moderator 16 provides the passageway from the interior of bag 14 to the exterior of the dispenser 30 by which composition 17 is discharged from dispenser 30. Flow moderator 16 comprises a conduit, in the form of a rigid cylindrical tube 38, and a dome-shaped head 39. Tube 38 and head 39 may be made from suitable plastics or metals. Head 39 has an axial, threaded bore 40 that receives threaded end 42 of tube 38. As shown in FIGS. 6 and 7, end 42 extends outwardly from the spherical surface of head 39 to provide a site for attaching an external catheter tube (not shown) in the event dispenser 30 is to be used to administer composition 17 to a remote location. The outer diameter of tube 38 is approximately the same as the diameter of bore 35 such that tube 38 may be inserted through bore 35 into bag 14 with tube 38 fitting snugly within bore 35 so as to form an essentially fluid tight seal with plug 15. Head 39 has a diameter slightly larger than the outer diameter of plug 15, and, as seen in FIG. 7, the flat side of head 39 fits against the top of plug 15.

Dispenser 30 also can include a flow moderator cap 44 which may be used to cover protruding end 42 of tube 38 when dispenser 30 is used without an external catheter tube connection. Cap 44 is crescent-shaped and has an axial threaded bore 46 that receives end 42. The curvature of its concave underside 35 matches the convexity of the top surface of head 39 so that the former fits tightly against the latter, as seen in FIG. 7. The outer diameter of cap 44 is the same as the outer diameter of membrane 12. Thus the hemispherical exterior of cap 44 provides a smooth, blunt surface that aligns with the exterior surface of membrane 12.

The components of the above-described dispensers may be made and assembled as follows. The inner, flexible bag with an arcuate upper edge may be injection molded from suitable polymer compositions by known techniques. The bag is then placed on a support means, such as a mandrel, and a suspension of the osmotically effective solute in an appropriate suspending medium is prepared. The supported bag is then dipped repeatedly in the suspension to the desired depth, with intervening drying periods, until a layer of osmotic solute of desired thickness is formed.

A solution of membrane material is then made and the supported, solute coated bag is dipped repeatedly into the solution to a depth just above the top edge of bag 14, with intervening drying periods, until an outer membrane of desired thickness is formed. The outer membrane may be prepared from cellulose-based polymers, such as cellulose acetate butyrate, cellulose acetate propionate and cellulose triacetate. Other polymers that may be used include acrylic polymers, such a polymethylmethacryate. The polymers may be used alone or as mixtures with each other. Ethyl cellulose may also be added to the polymers or mixtures of the polymers to provide presently preferred polymeric bases for the membrane coatings. The mixtures may contain polymer to ethyl cellulose in ratios generally in the range of 1:9-9:1, more often 1:5 to 5:1. Representative examples are those mixtures comprised of 1 part of polymethylmethacrylate to 1 part of ethyl cellulose, 1 part of polymetylymehacrylate to 3 parts of ethyl cellulose, and 5 parts of polymethylmethacrylate to 4 parts of ethyl cellulose. Cellulose polymers are soluble in various solvents in varying degrees. For example, cellulose acetate butyrate and cellulose triacetate are readily soluble in methylene chloride. However, use of this solvent is not preferred for regulatory and safety reasons. The celluloses are soluble in acetone, ethyl acetate, methyl acetate, mixtures of methylene chloride and isopropyl alcohol, mixtures of acetone and water, and mixtures of methyl and ethyl alcohol and ethyl acetate. Preferred solvents are acetone, acetone and water, and acetone and lower alkanols having 1-8 carbon atoms. Representative alcohols include methanol, ethanol, isopropyl alcohol, and the like.

Although methylene chloride is not a preferred solvent for reasons of safety, devices having an outer membrane of a cellulose-based polymer prepared from solvents other than methylene-chloride were prone to development of fissures at sharp edge regions of the devices described herein. In accord with one aspect of this invention, however, it has been surprisingly discovered that such problems can be avoided when the open end of the inner bag and/or the cap adapted for sealing the open end are characterized by an arcuate edge. In this manner, satisfactory devices such as those described herein having an outer membrane of a cellulose-based or acrylic polymer prepared from solvents other than methylene-chloride, such as acetone and acetone-based solvent systems, can be prepared.

The mandrel is then removed and a plug, which may be injection molded by known techniques, is glued into the open end of the bag. A head may be machined by known techniques if it is metal, or injection molded by known techniques if made from a synthetic polymer. The end of the capillary tube may be affixed within the bore by press-fitting, gluing, or other known techniques.

Alternatively, the plug may be glued into the open end of the bag prior to the solution of membrane material being coated upon the surface of the sealed inner bag and thereby encapsulating the polymer composition. Coating is accomplished by known in the art methods such as pan coating and fluidized spray coating.

The dispensers may be filled with fluid via the bore in the plug. For instance, the needle of a fluid loaded syringe may be inserted through the bore and the syringe's contents discharged into the bag. To ensure that a predetermined fluid pumping rate is achieved, it is desirable to completely fill bag with fluid. After the bag is filled, the tube of the flow moderator is inserted through the bore to the position shown in the figures. The tube functions as a capillary and inhibits loss of fluid from the dispensers even though they are subjected to substantial movement or tipped upside down.

The dispensers operate in the following manner. Once placed in an aqueous environment, such as within a body cavity or within body tissue, water from the environment is imbibed by the osmotic layer through the outer membrane at a rate determined by the osmotic activity of the osmotically effective solute, and the osmotic reflection coefficient, composition, thickness, and area of the outer membrane. The imbibed water causes the volume of the space between the inner surface of the outer membrane and the exterior of the inner bag (the space initially occupied by the osmotic layer) to increase. And since the outer membrane is shape-retaining, the imbibed water generates hydraulic pressure on the exterior of the fluid bag causing the bag to be squeezed inwardly. This squeezing forces fluid through the tube and out of the dispenser. Any air bubbles that were trapped within the bag during filling will tend to be located adjacent to the inner end of the plug or the inner surface of the bag, depending on the attitude of the dispenser. Therefore, these air bubbles are not likely to block the entrance to tube and interrupt or impede the flow of fluid therethrough.

Preferred membranes are those formed from cellulose acetate butyrate, cellulose acetate propionate, and polymethylacrylate, either alone or in mixtures with each other and optionally ethyl cellulose, and that are deposited out of acetone-based solvent systems. It has also been discovered that polymer-solvent compositions that are useful to prepare outer membranes for the devices described herein also have utility with respect to other osmotic devices and systems generally that utilize a semipermeable membrane. Representative osmotic devices and systems have been described, for example, in U.S. Pat. Nos. 4,503,030; 4,519,801; 4,522, 625; 4,553,973; 4,576,604; 4,578,075; 4,627,850; 4,777, 049; 4,783,337; 4,863,744; 4,940,465; 4,946,687; 4,948, 592; 5,019,396; 5,208,037; 5,232,705; 5,324,280; and 5,413,572, which are incorporated herein by reference.

The cellulose acetate butyrate, cellulose acetate propionate and polymethylmethacryate may be used alone or as mixtures with each other. Ethyl cellulose may also be added to the polymers or mixtures of the polymers to provide presently preferred polymeric bases for the membranes that are formed by depositing the polymers on the osmotic systems from compositions of the polymer and solvent. Preferred solvents are acetone, acetone and water, and acetone and lower alkanols having 1-8 carbon atoms. Representative alcohols include methanol, ethanol, isopropyl alcohol, and the like. Optionally, one or more additives selected from the group consisting of plasticizers and flux enhancers, such as those described previously herein may be added to the coating compositions. The lower alkanols may be straight or branched chain, and are illustrated by representative alcohols such as methanol, ethanol, isopropyl alcohol, and the like. Typically, the concentration of acetone in the solvent is at least 80% by volume, more often about 90%. The polymer concentration in the solvent is between 1-15% (w/v), and may range between 1%-10% (w/v), often 1%-5% (w/v). The coating compositions of the invention typically provide for formed semipermeable membrane coats exhibiting a water transmission rate (i.e., $K\pi \times 10^{-3}$) of between 1-60 cc·mil/cm²·hr, often 3-40 cc·mil/cm²·hr, as measured by standard methods using sodium chloride. The coats may be deposited on the osmotic cores by conventional methods, e.g., pan coating. For the particular devices described herein, the coat may be from 10-80% by weight of the bag coated with the osmotically-effective solute. For more general osmotic systems such as those described in the aforesaid patents, coatings of 1-50%, more often 1-30%, by weight of the weight of the bilayer drug/push composition cores is typical. For the general osmotic drug systems adapted for once-a-day administration, the coating compositions of this invention provide dosage forms with coated outer membranes that have 0-4 hour start up periods and permit about 90% of the drug to be delivered over 20 or more hours. For sustained release dosage forms intended for a twice-a-day administration, the membranes formed from the coating compositions of the invention allow for start-up times of 0-2 hours.

Particularly useful polymers for preparing the coating compositions of the invention are the cellulose acetate butyrate polymers having an acetyl content ranging from about 2%-30%, a butyrl content of about 17%-52% and a hydroxyl content of about 1%-5%, with number average molecular weights ranging from 20,000-60,000. Such polymers are available from the Eastman Chemical Company, Kingsport, Tenn., under the grade designations CAB-171, -321, -381, -500, -531, -551, and -553. Cellulose acetate propionates are available from the same company having acetyl content of 0.6%-2.5%, propionyl content of 42.5-46%, and hydroxyl content of 1.8-5%, and number average molecular weights of 15,000-75,000. Grade designations are CAP-482 and -504. The polymethylmethacrylates may include, for example, those sold under the trade name Plexiglass®, particularly Plexiglass® V-825 sold by Poly-One Corporation (previously M.A. Hanna Company), Lemont, Ill., USA, and Rohm and Haas, Philadelphia, Pa., USA. Ethyl cellulose may be obtained from a number of suppliers to the pharmaceutical industry, including that sold by the Dow Chemical Company under the trade name Ethocel®. Representative pharmaceutical grades may have viscosities in the range of 3-110 cP (measured as 5% solutions at 25 degrees Centigrade in an Ubbelohde viscometer with a solvent of 80% toluene and 20% alcohol) and an ethoxyl content of 48%-49.5%. The foregoing examples are illustrative and those skilled in the pharmaceutical formulation and manufacturing arts may select materials having different physical properties for a particular application.

The coating compositions may optionally include plasticizers and flux regulating agents such as described previously.

The coating compositions are prepared by conventional procedures. Polymer is mixed, along with any optional additives, with the selected solvent system and allowed to dissolve to form a coating solution. That solution is then applied to the osmotic systems by pan coating or the like. The coated systems typically are allowed to dry or dried under forced conditions to allow for formation of the solid, semipermeable membrane encapsulating the osmotic system or device.

The following examples are intended to further illustrate the above-described dispensers and their manufacture. The example is not intended to limit the invention in any way. Unless indicated otherwise, percentages and parts are by weight.

EXAMPLE 1

Cylindrical flexible bags (2.50 cm long, 4.01 mm I.D. and 4.62 mm O.D.) were injection molded at 176° C., $3.5 \times 10^3$ kPa, from an elastomeric styrene-butadiene copolymer (sold under the trade designation, KRATON 2104). The mold was designed to form bags having an arcuate edge with a radius of curvature of 0.047 inches at the open end of each bag.

Osmotic sleeves were prepared for each dispenser as follows. The components 64.5 wt % NaCl, 20 w % poly[ethylene oxide], molecular wt 600,000, 15 wt % poly[ethylene glycol] of molecular weight 20,000 and 0.5 wt % colloidal $SiO_2$, sold under the trade name CABOSIL were bulk blended in a Hobart mixer for 20 minutes at low speed. The homogenous powder blend was pressed into 0.6 cm tablets capable of being gravity fed into Arborg injection molding equipment. The osmotic sleeves (2.21 cm long, 4.87 mm I.D., and 5.89 mm O.D.) were formed from the tablets by injection molding at 149° C. $6.5 \times 10^3$ kPa.

Cylindrical plugs of KRATON™ styrene-butadiene copolymer were injection molded. The plugs were 0.5 cm long, had a 4.1 mm O.D., their lower surfaces were recessed hemispherically to a depth of 1.37 mm, and had a central axial bore 0.76 mm in diameter through the length of the plug.

The cylindrical flexible bags were dipped into a 15 wt % cyclohexane solution of the KRATON™ styrene-butadiene copolymer and were inserted into the osmotic sleeve. The arcuate surfaces of the plugs were coated with a glue bead of 15 wt % cyclohexane solution of the copolymer and a plug was inserted into the open end of each of the bags. A 22-gauge needle was inserted through the bore of each plug and the plugged bags were placed in an oven at 40° C. for 2 hours.

An outer semipermeable membrane was applied to the dispensers by pan coating or by coating with a Wurster coater. The membrane was a 4.5 wt % acetone solution of cellulose acetate butyrate (sold under the designation Eastman Kodak 171-15) and 0.5% of POLAXAMER 188 (brand name PLURONIC F68). The coating was applied to a thickness of 0.38 mm. The dispensers were then oven-dried at 55° C. for about 5-10 days.

Flow moderators were prepared for each dispenser as follows. Twenty-one gauge needle stock was cut into 2.36 cm lengths. Each length of tubing was circumferentially grooved with 15 grooves, equally spaced 0.3 mm apart along one end of the tube, such that a 4.3 mm distance beginning at one end of the tube is grooved. Caps were insert molded around the grooved portion of the tube 3 mm from the grooved end, from styreneacrylonitrile copolymer. The caps were hemispherical, 5.6 mm in diameter, with a 0.8 mm diameter diametrical bore. Hemispherical overcaps had a 6.5 mm O.D., were 4.3 mm in length with the bottom hemispherically recessed to a depth of 1.3 mm, had a 0.8 mm diameter diametrical bore through the length of the overcap, and were injection molded from ethylenevinyl-acetate copolymer. The overcaps were pressed onto the 3 mm grooved extension of the tube.

The dispenser was filled with blue dye and tested in vitro to determine the release rate as a function of time. The release of a prior art device prepared with the same specifications except that the inner bag was formed with a 90° angle at the edge of the open end, as in the prior art device of FIG. 4. The release profiles of both dispensers is shown in FIG. 8, where the device of the invention is represented by the dotted bars and the prior art, comparative device by the bars filled with dashes. As can be seen the development of cracks in the seal in the region of the inner bag edge and the outer membrane results in a decrease in release rate of the prior art device. The device of the invention maintained the release rate over the testing period.

EXAMPLE 2

The foregoing procedure is repeated using cellulose acetate propionate as the polymer. Release profiles for the dispenser are satisfactory and the absence of cracks in the seal region is noted.

EXAMPLE 3

The acetone in the coating solution of Example 1 is replaced with equivalent quantities of acetone-water (90:10), acetone-methanol (90:10), and acetone-ethanol (90:10), and the procedures of the Example repeated in other respects. Devices prepared therefrom are satisfactory and the absence of cracks in the seal region is noted.

Although the invention has been described with respect to particular embodiments, it will be apparent to those skilled in the art that various changes and modifications can be made without departing from the invention. All such changes and modifications are considered to be within the scope and spirit of the present invention as defined by the following claims.

What is claimed is:

1. A dispenser comprising:
   (i) a flexible container having a closed end and an opposed open end;
   (ii) an osmotically-effective solute composition encapsulating at least a portion of the container;
   (iii) a shape-retaining, semipermeable membrane encapsulating the osmotically-effective solute composition and the flexible container;
   (iv) a cap having a surface adapted for sealing engagement with the open end of the container;
   (v) a port extending from the interior of the container and through the cap;
   wherein the open end of the flexible container terminates in an edge, and wherein a portion of said edge in contact with the semipermeable membrane and adjacent a junction of said edge with the semipermeable membrane is arcuate.

2. The dispenser of claim 1, wherein the arcuate edge has a radius of curvature between 0.01 inches (0.254 mm) and 0.09 inches (2.29 mm).

3. The dispenser of claim 2, wherein the arcuate edge has a radius of curvature between 0.01 inches (0.254 mm) and 0.08 inches (2.03 mm).

4. The dispenser of claim 2, wherein the arcuate edge has a radius of curvature between 0.01 inches (0.254 mm) and 0.07 inches (1.78 mm).

5. The dispenser of claim 1 wherein the semipermeable membrane comprises a polymer selected from the group consisting of cellulose acetate butyrate, cellulose acetate propionate, polymethylmethacrylate, mixtures thereof, and mixtures of any of the foregoing with ethyl cellulose.

6. The dispenser of claim 5 wherein the polymer is selected from the group consisting of cellulose acetate butyrate and mixtures of cellulose acetate butyrate and ethyl cellulose.

7. The dispenser of claim 5 wherein the polymer is selected from the group consisting of cellulose acetate propionate and mixtures of cellulose acetate propionate and ethyl cellulose.

8. The dispenser of claim 5 wherein the polymer is selected from the group consisting of polymethylmethacrylate and mixtures of polymethylmethacrylate and ethyl cellulose.

9. The dispenser of claim 5 wherein the semipermeable membrane further comprises a solvent selected from the group consisting of acetone, mixtures of acetone and water and mixtures of acetone and lower alkanols having 1-8 carbon atoms, and optionally one or more additives selected from the group consisting of plasticizers and flux enhancers.

10. The dispenser of claim 9 wherein the solvent is selected from the group consisting of acetone, a mixture of acetone and water, a mixture of acetone and methanol, and a mixture of acetone and ethanol.

11. The dispenser of claim 10 wherein the semipermeable membrane exhibits a water transmission rate between 3 and 45 cc·mil/cm²·hr.

12. The dispenser of claim 9 wherein the semipermeable membrane exhibits a water transmission rate between 1 and 60 cc·mil/cm²·hr.

13. The dispenser of claim 1, further comprising a plug fitted into the open end of the container.

14. The dispenser of claim 13, wherein the plug has a hemispherically recessed surface in a bottom end thereof.

* * * * *